US011022600B2

(12) United States Patent
Suzuki et al.

(10) Patent No.: US 11,022,600 B2
(45) Date of Patent: Jun. 1, 2021

(54) METHOD FOR ASSESSING STATE OF DIFFERENTIATION OF CELLS

(71) Applicant: Shimadzu Corporation, Kyoto (JP)

(72) Inventors: Takashi Suzuki, Osaka (JP); Norio Nakatsuji, Kyoto (JP); Hirofumi Suemori, Kyoto (JP); Shinichiro Chuma, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 512 days.

(21) Appl. No.: 15/307,948

(22) PCT Filed: Apr. 21, 2015

(86) PCT No.: PCT/JP2015/062128
§ 371 (c)(1),
(2) Date: Oct. 31, 2016

(87) PCT Pub. No.: WO2015/166845
PCT Pub. Date: Nov. 5, 2015

(65) Prior Publication Data
US 2017/0052171 A1 Feb. 23, 2017

(30) Foreign Application Priority Data

May 1, 2014 (JP) .............................. JP2014-094507

(51) Int. Cl.
*G01N 33/50* (2006.01)
*C12Q 1/04* (2006.01)

(52) U.S. Cl.
CPC ........... *G01N 33/5005* (2013.01); *C12Q 1/04* (2013.01); *G01N 2560/00* (2013.01)

(58) Field of Classification Search
None
See application file for complete search history.

(56) References Cited

U.S. PATENT DOCUMENTS 9,500,650 B2 * 11/2016 Tateno ............. G01N 33/56966
2011/0117645 A1 5/2011 Yasuda et al.
(Continued)

FOREIGN PATENT DOCUMENTS

EP 2 275 531 A1 1/2011
JP 2004-313184 A 11/2004
(Continued)

OTHER PUBLICATIONS

Jones, S.P. et al. 2013. Published online Sep. 15, 2013. The kynurenine pathway in stem cell biology. International Journal of Tryptophan Research 6: 57-66. specif, pp. 59, 62, 64.*

(Continued)

*Primary Examiner* — David W Berke-Schlessel
(74) *Attorney, Agent, or Firm* — Oblon, McClelland, Maier & Neustadt, L.L.P.

(57) ABSTRACT

In the present invention, for test cells which are either stem cells whose state of differentiation is unknown or cells obtained from stem cells by differentiation induction, an LC-MS or GC-MS analysis is performed on culture supernatants collected from a culture dish of the test cells and a culture dish of control cells whose state of differentiation is known, and the state of differentiation of the test cells is assessed based on the amount, determined as a result of the aforementioned analysis, of at least one compound selected from the group of putrescine, kynurenine, cystathionine, ascorbic acid, riboflavin, pyruvic acid, serine, cysteine, threonic acid, citric acid, and orotic acid in both the culture supernatant of the test cells and the culture supernatant of the control cells.

19 Claims, 6 Drawing Sheets

(56) References Cited

U.S. PATENT DOCUMENTS

2013/0202574 A1  8/2013  Greene et al.
2015/0361411 A1  12/2015  Greene et al.

FOREIGN PATENT DOCUMENTS

| | | |
|---|---|---|
| JP | 2006-42663 A | 2/2006 |
| WO | WO 2011/139907 A2 | 11/2011 |
| WO | WO-2012123401 A1 * 9/2012 ........... C12N 5/0637 |
| WO | WO 2013/065302 A1 | 5/2013 |

OTHER PUBLICATIONS

EngMT. Tateno, H. et al. Undifferentiated cell detection method and complex carbohydrate detection method. International Patent Application Publication No. WO 2013/065302 A1. Published May 10, 2013. pp. 1-56.*

Cezar, G.G. et al. Identification of small molecules from human embryonic stem cells using metabolomics. Stem Cells and Development 16: 869-882. specif, pp. 869, 870, 876.*

Australian Office Action dated Jun. 27, 2017 in Patent Application No. 2015254267.

Extended European Search Report dated Mar. 23, 2017 in Patent Application No. 15785591.7.

International Search Report dated Jun. 30, 2015 in PCT/JP2015/062128 filed Apr. 21, 2015.

International Preliminary Report on Patentability and Written Opinion dated Nov. 1, 2016 in PCT/JP2015/062128 filed Apr. 21, 2015 (with English translation).

* cited by examiner

Fig. 4

| Components |
|---|
| Amino Acids |
| Glycine |
| L-Alanine |
| L-Arginine hydrochloride |
| L-Asparagine-H2O |
| L-Aspartic acid |
| L-Cysteine hydrochloride-H2O |
| L-Cystine 2HCl |
| L-Glutamic Acid |
| L-Glutamine |
| L-Histidine hydrochloride-H2O |
| L-Isoleucine |
| L-Leucine |
| L-Lysine hydrochloride |
| L-Methionine |
| L-Phenylalanine |
| L-Proline |
| L-Serine |
| L-Threonine |
| L-Tryptophan |
| L-Tyrosine disodium salt dihydrate |
| L-Valine |
| Vitamins |
| Biotin |
| Choline chloride |
| D-Calcium pantothenate |
| Folic Acid |
| Niacinamide |
| Pyridoxine hydrochloride |
| Riboflavin |
| Thiamine hydrochloride |
| Vitamin B12 |
| i-Inositol |
| Inorganic Salts |
| Calcium Chloride (CaCl2) (anhyd.) |
| Cupric sulfate (CuSO4-5H2O) |
| Ferric Nitrate (Fe(NO3)3"9H2O) |
| Ferric sulfate (FeSO4-7H2O) |
| Magnesium Chloride (anhydrous) |
| Magnesium Sulfate (MgSO4) (anhyd.) |
| Potassium Chloride (KCl) |
| Sodium Bicarbonate (NaHCO3) |
| Sodium Chloride (NaCl) |
| Sodium Phosphate dibasic (Na2HPO4) anhydrous |
| Sodium Phosphate monobasic (NaH2PO4-H2O) |

Fig. 5

| | Compound |
|---|---|
| 1 | Glycine |
| 2 | L-Alanine |
| 3 | L-Valine |
| 4 | L-Leucine |
| 5 | L-Isoleucine |
| 6 | L-Proline |
| 7 | L-Serine |
| 8 | L-Threonine |
| 9 | L-Methionine |
| 10 | L-Phenylalanine |
| 11 | L-Tyrosine disodium salt dihydrate |
| 12 | L-Tryptophan |
| 13 | L-Asparagine-H2O |
| 14 | L-Glutamine |
| 15 | L-Histidine hydrochloride-H2O |
| 16 | L-Lysine hydrochloride |
| 17 | L-Arginine hydrochloride |
| 18 | L-Aspartic acid |
| 19 | L-Glutamic Acid |
| 20 | L-Cysteine hydrochloride-H2O |
| 21 | L-Cystine 2HCl |
| 22 | Sodium Pyruvate |
| 23 | Pipecolic acid |
| 24 | GABA |
| 25 | D-Glucose (Dextrose) |
| 26 | Biotin |
| 27 | Niacinamide |
| 28 | i-Inositol |
| 29 | D-Calcium pantothenate |
| 30 | Riboflavin |
| 31 | Lipoic Acid |
| 32 | Pyridoxine hydrochloride |
| 33 | Thiamine hydrochloride |
| 34 | Folic Acid |
| 35 | Choline chloride |
| 36 | Vitamin B12 |
| 37 | L-Ascorbic acid 2-phosphate magnesium salt |
| 38 | DL-alpha-Tocopherol Acetate |
| 39 | Putrescine 2HCl |
| 40 | Hypoxanthine Na |

Fig 6

| | |
|---|---|
| 41 | Thymidine |
| 42 | Linoleic Acid |
| 43 | Arachidonic Acid |
| 44 | Linolenic Acid |
| 45 | Myristic Acid |
| 46 | Oleic Acid |
| 47 | Palmitic Acid |
| 48 | Palmitoleic Acid |
| 49 | Stearic Acid |
| 50 | Cholesterol |
| 51 | Reduced glutathione |
| 52 | Insulin |
| 53 | Ethyl Alcohol 100% |
| 54 | β-Mercaptoethanol |
| 55 | Pluronic F-68 |
| 56 | Tween 80® |
| 57 | Phenol Red |
| 58 | BSA fraction V |
| 59 | Bovine holo transferrin |
| 60 | TGFβ1 |
| 61 | zbFGF |
| 62 | Calcium Chloride ($CaCl_2$) (anhyd.) |
| 63 | Cupric sulfate ($CuSO_4$-$5H_2O$) |
| 64 | Ferric Nitrate ($Fe(NO_3)_3$"$9H_2O$) |
| 65 | Ferric sulfate ($FeSO_4$-$7H_2O$) |
| 66 | Magnesium Chloride (anhydrous) |
| 67 | Magnesium Sulfate ($MgSO_4$) (anhyd.) |
| 68 | Potassium Chloride (KCl) |
| 69 | Sodium Bicarbonate ($NaHCO_3$) |
| 70 | Sodium Chloride (NaCl) |
| 71 | Sodium Phosphate dibasic ($Na_2HPO_4$) anhydrous |
| 72 | Sodium Phosphate monobasic ($NaH_2PO_4$-$H_2O$) |
| 73 | Zinc sulfate ($ZnSO_4$-$7H_2O$) |
| 74 | Sodium Selenite |
| 75 | LiCl |
| 76 | PBS |
| 77 | Trace Elements B |
| 78 | Trace Elements C |

METHOD FOR ASSESSING STATE OF DIFFERENTIATION OF CELLS

TECHNICAL FIELD

The present invention relates to a method for assessing the state of differentiation of cells.

BACKGROUND ART

Conventionally, a method which uses the technique of immunostaining (for example, see Patent Literature 1) and a method which quantitatively determines the level of expression of a marker gene (for example, see Patent Literature 2) have been widely used in order to assess the state of differentiation of cells.

In the method which uses immunostaining, the cells to be subjected to the assessment (e.g. pluripotent stem cells) are fixed with paraformaldehyde (or other agents) and subjected to an antigen-antibody reaction. In this reaction, SSEA-4 and TRA1-60 have been commonly used as the antibody for determining whether or not the pluripotent stem cells are in the undifferentiated state (for example, see Patent Literature 1). Subsequently, a secondary antibody which can be bound to the aforementioned antibody is added to the cells. After that, a fluorescent label (or similar agent) which has been previously given to the secondary antibody is detected. Based on the detection result, it is possible to make an assessment on whether or not an antigen for the aforementioned antibody is present on the cells, i.e. whether or not the cells in question are in the undifferentiated state.

In the method which uses quantitative determination of the level of expression of a marker gene, for example, mRNA is extracted from the pluripotent stem cells and converted into cDNA using transcriptase. After that, the marker gene is amplified by PCR (polymerase chain reaction). In this reaction, NANOG are POU5F1 (OCT3/4) are widely used as the marker gene for determining whether or not pluripotent stem cells are in the undifferentiated state (for example, see Non Patent Literature 1). The obtained PCR product is detected by electrophoresis, or with a real-time PCR device, to determine the amount of expression of the marker gene in the cells. Based on the determination result, an assessment is made on whether or not the cells are in the undifferentiated state.

CITATION LIST

Patent Literature

Patent Literature 1: JP 2004-313184 A
Patent Literature 2: JP 2006-042663 A

Non Patent Literature

Non Patent Literature 1: *Nature Biotechnology*, 2007, Vol. 25, pp. 803-816

SUMMARY OF INVENTION

Technical Problem

However, in any of these conventional assessment methods, an invasive treatment needs to be performed on the cells. Therefore, after the assessment on the state of differentiation is completed, the cells which have undergone the assessment process cannot be used for other purposes; for example, they cannot be used as the cell source for regenerative medicine. Furthermore, it is impossible to assess a change of the same sample (i.e. cells in the same culture dish) over time. In order to assess the temporal change in their state of differentiation, a complex task is required, such as the concurrent culturing of the cells using a plurality of culture dishes.

The present invention has been developed in view of the previously described points. Its objective is to provide a method for assessing the state of differentiation of cells in a non-invasive manner.

Solution to Problem

As a result of intensive studies, the present inventors have discovered that the amount of putrescine, kynurenine, cystathionine, ascorbic acid, riboflavin, pyruvic acid, serine, cysteine, threonic acid, citric acid, and orotic acid present in a culture supernatant change depending on the state of differentiation of the cells. Thus, the present invention has been conceived.

The cell differentiation state assessment method according to the present invention developed for solving the previously described problem is a method for assessing the state of differentiation of test cells based on the amount of a specified substance in a culture supernatant of the test cells, the test cells being either stem cells whose state of differentiation is unknown or cells obtained from stem cells by differentiation induction, where:

the specified substance is at least one compound selected from the group of putrescine, kynurenine, cystathionine, ascorbic acid, riboflavin, pyruvic acid, serine, cysteine, threonic acid, citric acid, and orotic acid.

In the cell differentiation state assessment method according to the present invention, for example, the state of differentiation of the test cells may be assessed by comparing the amount of the specified substance in a culture supernatant of the test cells and the amount of the specified substance in a culture supernatant of control cells whose state of differentiation is known.

In the cell differentiation state assessment method according to the present invention, the stem cells may be pluripotent stem cells, such as ES cells (embryonic stem cells) or iPS cells (induced pluripotent stem cells).

In the cell differentiation state assessment method according to the present invention, the amount of the specified substance in the culture supernatant may be quantitatively determined by mass spectrometry.

Advantageous Effects of the Invention

By the cell differentiation state assessment method according to the present invention, it is possible to assess the state of differentiation of cells in a non-invasive manner without breaking the cells as in the conventional methods. Therefore, after the assessment on the state of differentiation is completed, the test cells can be used for other purposes, e.g. as the cell source for regenerative medicine. In the case of assessing the change in the state of differentiation over time, it is unnecessary to perform any complex task as in the conventional case, such as the concurrent culturing of the cells using a plurality of culture dishes. The change in the state of differentiation over time can be easily assessed for cells in the same culture dish.

BRIEF DESCRIPTION OF DRAWINGS

FIG. 4 is a table showing the components of DMEM/F12.

FIG. 5 is the first part of a table showing the components of mTeSR1.

FIG. 6 is the second part of the table showing the components of mTeSR1.

DESCRIPTION OF EMBODIMENTS

In the cell differentiation state assessment method according to the present invention, the state of differentiation of test cells is assessed based on the amount of a biomarker in a culture supernatant of the test cells, where at least one compound selected from the group of putrescine, kynurenine, cystathionine, ascorbic acid, riboflavin, pyruvic acid, serine, cysteine, threonic acid, citric acid, and orotic acid is used as the biomarker.

As the test cells, stem cells may be used, typical examples of which are pluripotent stem cells, such as ES cells and iPS cells. Cells obtained from the stem cells by differentiation induction may also be used as the test cells. As the culture medium for culturing these kinds of test cells, any culture medium generally used for the culturing of stem cells can be used, such as DMEM/F12 or culture media containing DMEM/F12 as the main component (e.g. mTeSR1). FIG. 4 shows the components of DMEM/F12.

As the method for determining the amount of the biomarker in a culture supernatant, a quantitative analysis by mass spectrometry, and particularly, a quantitative analysis using a liquid chromatogram mass spectrometer (LC-MS) or gas chromatograph mass spectrometer (GC-MS) can suitably, but not exclusively, be used. As another example, an agent or the like which makes each biomarker develop a specific color or emit specific light may be added to the culture supernatant, in which case the amount of the biomarker can be determined based on the intensity of the coloring or emission of light.

EXAMPLE

Figure 1:
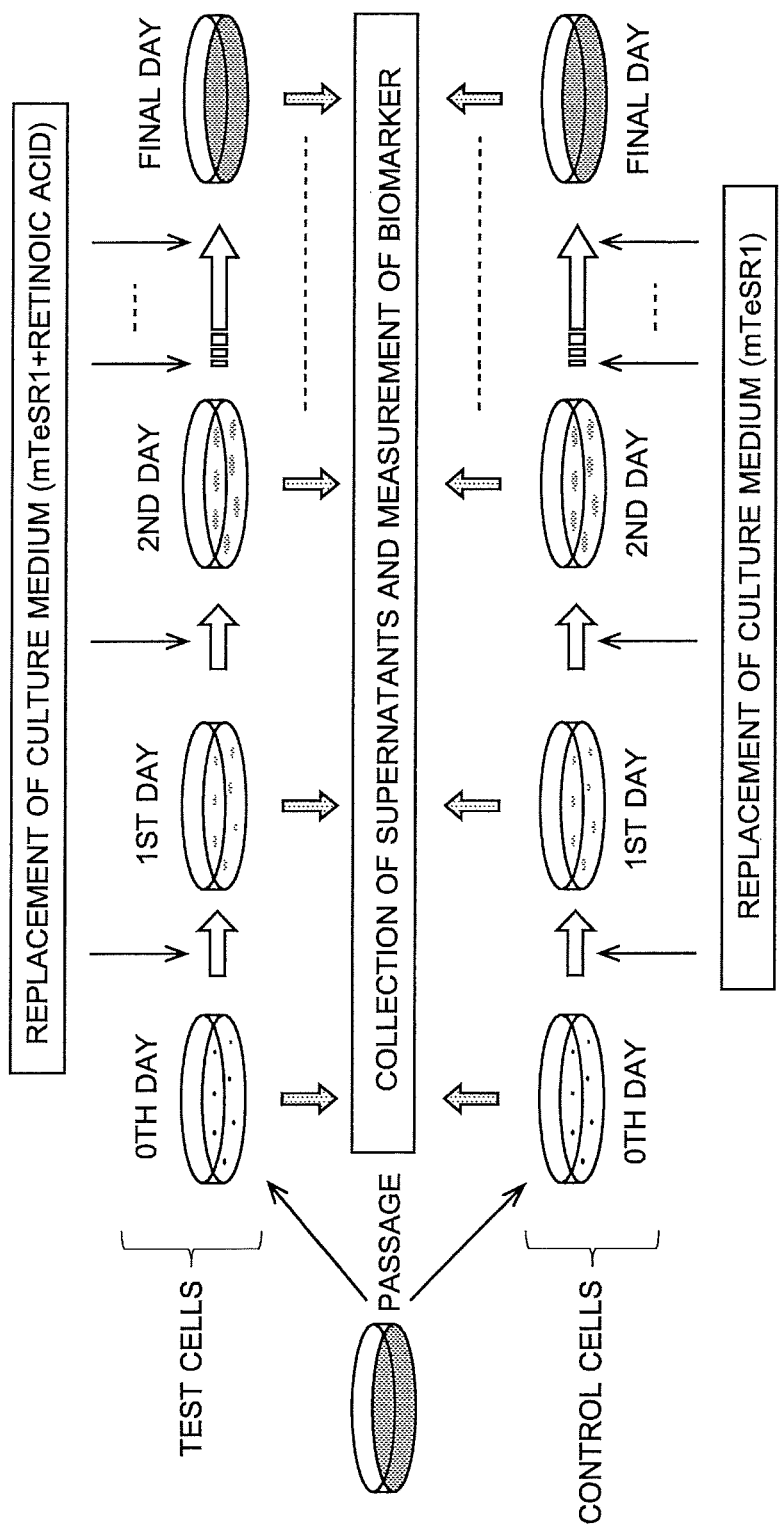
FIG. 1 is a model diagram illustrating the cell differentiation state assessment method in one example of the present invention.

One example of the assessment on the state of differentiation of cells by the method according to the present invention is hereinafter described. FIG. 1 is a model diagram showing the process steps of the cell differentiation state assessment method the present example.

In the present example, two kinds of human ES cell lines, KhES-1 and KhES-3, were used. Cells obtained by giving a differentiation induction stimulus to each human ES cell line were used as test cells, while the same human ES cell line maintained in the undifferentiated state were used as control cells. Hereinafter, the steps from the culturing of the cells to the analysis of the culture supernatant in the present example are described.

[Culturing of Control Cells and Collection of Culture Supernatants]

The aforementioned KhES-1 line was subcultured in four culture dishes (60 mm in diameter) coated with BioCoat Matrigel® (Corning International K.K.). (For simplification, only one culture dish is shown in FIG. 1). As the culture medium, mTeSR1 (modified Tenneille Serum Replacer 1) was used. The culture medium was replaced every day. The components of mTeSR1 are as shown in FIGS. 5 and 6. The KhES-3 line was also similarly subcultured in four culture dishes. With the first day of the subculturing (passage) of the cells counted as the zeroth day, the culturing was continued until the cells reached confluence. Every day, when the culture medium was replaced, the culture supernatant was collected from each culture dish as the sample for mass spectrometry. For the zeroth day of the culturing, mTeSR1 was directly used as the sample for mass spectrometry.

[Culturing of Test Cells and Collection of Culture Supernatants]

The aforementioned KhES-1 line was subcultured in four culture dishes (60 mm in diameter) coated with Matrigel. (For simplification, only one culture dish is shown in FIG. 1). As the culture medium, mTeSR1 was used. With the culture medium replaced every day, the culturing was continued until the cells reached confluence. The KhES-3 line was also similarly subcultured in four culture dishes. With the first day of the passage counted as the zeroth day, when the culture medium was replaced on the second and subsequent days, the old medium was replaced by mTeSR1 with retinoic acid added to the final concentration of 0.1 µM in order to give a differentiation induction stimulus. Every day, when the culture medium was replaced, the culture supernatant was collected from each culture dish as the sample for mass spectrometry. For the zeroth day of the culturing, mTeSR1 was directly used as the sample for mass spectrometry.

[Sample Pretreatment]

As the internal standard material, isopropylmalic acid was added to each of the samples, which were subsequently treated with an extraction solution (methanol, chloroform, and water mixed at a ratio of 2.5:1:1) to remove proteins. After the extraction, the supernatant was collected and dried.

[GC-MS Analysis]

Each of the samples pretreated in the previously described manner was incubated in a pyridine solution containing methoxyamine hydrochloride to methoximate the compounds in the sample. Additionally, MSTFA (N-Methyl-N-trimethylsilyltrifluoroacetamide) was added to each sample to trimethylsilylate the compounds in the sample. After these derivatization treatments, the samples were subjected to a GC-MS analysis. For the analysis of the measured results, the "GCMS Metabolites Database Ver. 2", produced by Shimadzu Corporation, was used. This database is a collection of data obtained by conducting GC-MS analyses on the standard products of various compounds subjected to derivatization treatments similar to the previously described one. The criteria used for the identification of the compounds were whether or not the difference between the retention index (a numerical value showing a relative retention time) specified in the database and the retention index of a derivatized compound in the sample was within a range of ±5, as well as whether or not both the target ion and confirmation ion designated in the database were detected for the derivatized compound in the sample. The quantitative determination of the compounds was performed by calculating the area of a mass chromatogram created for an ion characteristic of each derivatized compound in the sample according to the conditions specified in the database.

[LC-MS Analysis]

An appropriate amount of ultrapure water (Milli-Q® Water, Merck KGaA) was added to each of the samples pretreated in the previously described manner, and the obtained solutions were subjected to an LC-MS analysis. In the LC-MS analysis, the compounds in each sample were temporally separated by gradient elution using a reversed-phase separation column, and were subsequently subjected to a mass spectrometry in the multiple reaction monitoring mode. The analysis conditions in the MRM mode were previously set using standard products of the compounds. The criterion used for the identification of the compounds was whether or not the difference between the retention time of the standard product and that of a compound in the sample was within a range of ±0.1 minutes. The quantitative determination of the compounds was performed by calculating the area of a mass chromatogram created for an ion characteristic of each compound in the sample.

For the culture supernatants collected on the final day of the culturing (i.e. the culture supernatants sampled from the culture dishes which had reached confluence), the quantity value (area value) of each compound determined by the previously described GC-MS and LC-MS analyses was divided by the quantity value (area value) of the internal standard material, and the obtained value was adopted as the index value of the amount of each compound in the culture supernatant. Then, for each of the control and test cells, an average of the index values obtained from the results of the GC-MS and LC-MS analyses performed on the culture supernatants collected from the four culture dishes was calculated. Using the averages of the index values, the control cells and test cells were compared with each other in terms of the amount of each compound. Specifically, with A denoting the average of the index values calculated for the control cells and B denoting the average of the index values calculated for the test cells, if either A/B or B/A was equal to or greater than 1.2, and if P<0.05 in Student's t-test, it was concluded that there was a significant difference in the amount of the compound in question between the culture supernatant of the control cells and that of the test cells.

Tables 1-4 show compounds which were judged to have a significant difference in amount between the culture supernatant of the control cells and that of the test cells. In those tables, "E" denotes exponential in decimal; for example, "1.326E-02" means "$1.326 \times 10^{-2}$".

The following Tables 1 and 2 show compounds whose amount in the culture supernatant of the control cells was determined to be higher than in the culture supernatant of the test cells. Specifically, Table 1 is the result obtained for the KhES-1 line, while Table 2 is the result obtained for the KhES-3 line. The "variation" in these tables means the aforementioned A/B value, i.e. the ratio of the "average of the index values calculated for the control cells" to the "average of the index values calculated for the test cells".

TABLE 1

| Biomarker | Control Cells | | Test Cells | | Variation | P-Value |
| | Average | Standard Deviation | Average | Standard Deviation | | |
|---|---|---|---|---|---|---|
| putrescine | 1.326E−02 | 7.297E−04 | 1.454E−03 | 3.235E−04 | 9.12 | 5.70E−06 |
| cystathionine | 5.328E−03 | 7.375E−04 | 7.143E−04 | 1.409E−04 | 7.46 | 8.19E−04 |
| kynurenine | 2.877E−02 | 2.619E−03 | 1.559E−03 | 2.933E−04 | 18.45 | 2.12E−04 |
| ascorbic acid | 1.393E−01 | 2.639E−02 | 4.663E−03 | 4.962E−03 | 29.87 | 1.57E−03 |
| riboflavin | 1.712E−03 | 2.108E−04 | 1.063E−03 | 9.115E−05 | 1.61 | 4.54E−03 |

TABLE 2

| Biomarker | Control Cells | | Test Cells | | Variation | P-Value |
| | Average | Standard Deviation | Average | Standard Deviation | | |
|---|---|---|---|---|---|---|
| putrescine | 6.616E−03 | 7.919E−04 | 1.815E−03 | 4.021E−04 | 3.64 | 2.31E−04 |
| cystathionine | 3.086E−03 | 6.527E−04 | 5.741E−04 | 2.911E−04 | 5.37 | 1.88E−03 |
| kynurenine | 4.610E−02 | 1.613E−02 | 3.893E−03 | 1.171E−03 | 11.84 | 1.33E−02 |
| ascorbic acid | 1.405E−01 | 4.202E−02 | 3.103E−02 | 3.696E−02 | 4.53 | 8.14E−03 |
| riboflavin | 1.907E−03 | 1.583E−04 | 1.477E−03 | 1.902E−04 | 1.29 | 1.39E−02 |

The following Tables 3 and 4 show compounds whose amount in the culture supernatant of the test cells was determined to be higher than in the culture supernatant of the control cells. Specifically, Table 3 is the result obtained for the KhES-1 line, while Table 4 is the result obtained for the KhES-3 line. The "variation" in these tables means the aforementioned B/A value, i.e. the ratio of the "average of the index values calculated for the test cells" to the "average of the index values calculated for the control cells".

TABLE 3

| Biomarker | Control Cells | | Test Cells | | Variation | P-Value |
| | Average | Standard Deviation | Average | Standard Deviation | | |
| --- | --- | --- | --- | --- | --- | --- |
| pyruvic acid | 9.939E−02 | 1.315E−02 | 2.731E−01 | 1.397E−02 | 2.75 | 1.89E−06 |
| serine | 4.908E−02 | 1.383E−03 | 6.871E−02 | 1.056E−03 | 1.40 | 1.01E−06 |
| cysteine | 1.131E−01 | 4.911E−03 | 1.549E−01 | 1.036E−02 | 1.37 | 1.44E−03 |
| threonic acid | 5.549E−02 | 1.948E−03 | 9.306E−02 | 1.987E−03 | 1.68 | 1.71E−07 |
| orotic acid | 4.814E−03 | 4.869E−04 | 9.219E−03 | 6.354E−04 | 1.92 | 5.16E−05 |
| citric acid | 4.100E−02 | 2.967E−03 | 9.447E−02 | 4.738E−03 | 2.30 | 6.71E−06 |

TABLE 4

| Biomarker | Control Cells | | Test Cells | | Variation | P-Value |
| | Average | Standard Deviation | Average | Standard Deviation | | |
| --- | --- | --- | --- | --- | --- | --- |
| pyruvic acid | 9.817E−02 | 1.716E−02 | 1.801E−01 | 5.300E−02 | 1.83 | 4.79E−02 |
| serine | 4.335E−02 | 8.250E−03 | 5.933E−02 | 2.793E−03 | 1.37 | 2.47E−02 |
| cysteine | 1.587E−01 | 1.211E−02 | 2.130E−01 | 2.247E−02 | 1.34 | 9.64E−03 |
| threonic acid | 6.122E−02 | 1.360E−03 | 8.355E−02 | 1.161E−02 | 1.36 | 3.01E−02 |
| orotic acid | 2.822E−03 | 2.978E−04 | 6.322E−03 | 8.118E−04 | 2.24 | 1.58E−03 |
| citric acid | 4.410E−02 | 1.332E−02 | 8.086E−02 | 5.189E−03 | 1.83 | 7.31E−03 |

These results demonstrate that each of the compounds listed in Tables 1-4 shows a change in the amount of metabolic expenditure inside the cells and/or the amount of secretion to the outside of the cells as a result of the differentiation induction, and therefore, can be used as a biomarker for assessing the state of differentiation of the cells. For example, consider the case where the test cells are stem cells and whether or not these cells are maintained in the undifferentiated state is unknown, while the control cells are stem cells which are unmistakably in the undifferentiated state. For any of the compounds listed in Tables 1 and 2, if the ratio of the "amount in the culture supernatant of the control cells" to the "amount in the culture supernatant of the test cells" is equal to or higher than a predetermined threshold, it is possible to conclude that the test cells are not in the undifferentiated state. Similarly, for any of the compounds listed in Tables 3 and 4, if the ratio of the "amount in the culture supernatant of the test cells" to the "amount in the culture supernatant of the control cells" is equal to or higher than a predetermined threshold, it is possible to conclude that the test cells are not in the undifferentiated state.

As opposed to the previous case, the control cells may also be cells which are unmistakably differentiated. In this case, for any of the compounds listed in Tables 1 and 2, if the ratio of the "amount in the culture supernatant of the test cells" to the "amount in the culture supernatant of the control cells" is equal to or higher than a predetermined threshold, it is possible to conclude that the test cells are in the undifferentiated state. Similarly, for any of the compounds listed in Tables 3 and 4, if the ratio of the "amount in the culture supernatant of the control cells" to the "amount in the culture supernatant of the test cells" is equal to or higher than a predetermined threshold, it is possible to conclude that the test cells are in the undifferentiated state.

Consider another example in which the test cells are differentiation-induced cells derived from stem cells and whether or not undifferentiated cells remain is unknown, while the control cells are cells which are unmistakably undifferentiated. For any of the compounds listed in Tables 1 and 2, if the ratio of the "amount in the culture supernatant of the test cells" to the "amount in the culture supernatant of the control cells" is equal to or higher than a predetermined threshold, it is possible to conclude that undifferentiated cells are mixed in the test cells. Similarly, for any of the compounds listed in Tables 3 and 4, if the ratio of the "amount in the culture supernatant of the control cells" to the "amount in the culture supernatant of the test cells" is equal to or higher than a predetermined threshold, it is possible to conclude that undifferentiated cells are mixed in the test cells.

Consider yet another example in which the test cells are differentiation-induced cells derived from stem cells and whether or not undifferentiated cells remain is unknown, while the cells used as the control cells are unmistakably differentiated as opposed to the previous example. For any of the compounds listed in Tables 1 and 2, if the ratio of the "amount in the culture supernatant of the test cells" to the "amount in the culture supernatant of the control cells" is equal to or higher than a predetermined threshold, it is possible to conclude that undifferentiated cells are mixed in the test cells. Similarly, for any of the compounds listed in Tables 3 and 4, if the ratio of the "amount in the culture supernatant of the control cells" to the "amount in the culture supernatant of the test cells" is equal to or higher than a predetermined threshold, it is possible to conclude that undifferentiated cells are mixed in the test cells. Regardless of which method is used for the determination, the levels of amount of the compounds in the culture supernatant of the control cells do not need to be simultaneously measured with those of the test cells; instead, previously measured data may be used.

Among the compounds listed in Tables 1-4, putrescine, cystathionine, kynurenine and ascorbic acid, which were more abundant in the culture supernatant of the control cells than in the supernatant of the test cells, showed a considerable change in the amount, with variation values of 3.00 or higher (see Tables 1 and 2). Accordingly, it is most likely that these compounds are particularly suitable as a biomarker which indicates that the test cells are in the undifferentiated state, or which indicates that undifferentiated cells are mixed in the test cells.

Figure 2:
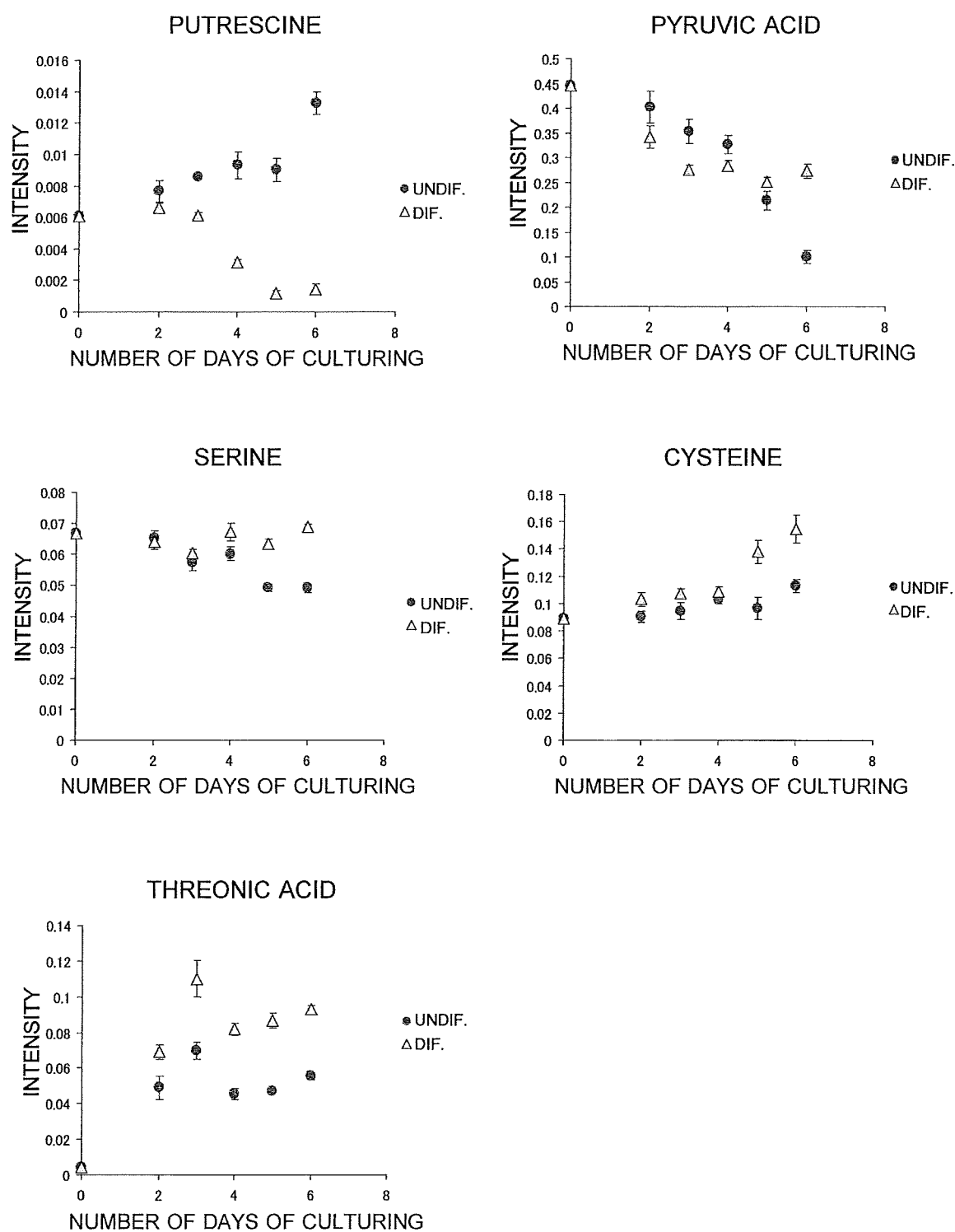
FIG. 2 is a graph showing a temporal change in the amount of various substances determined by a GC-MS analysis of a culture supernatant in the aforementioned example.
Figure 3:
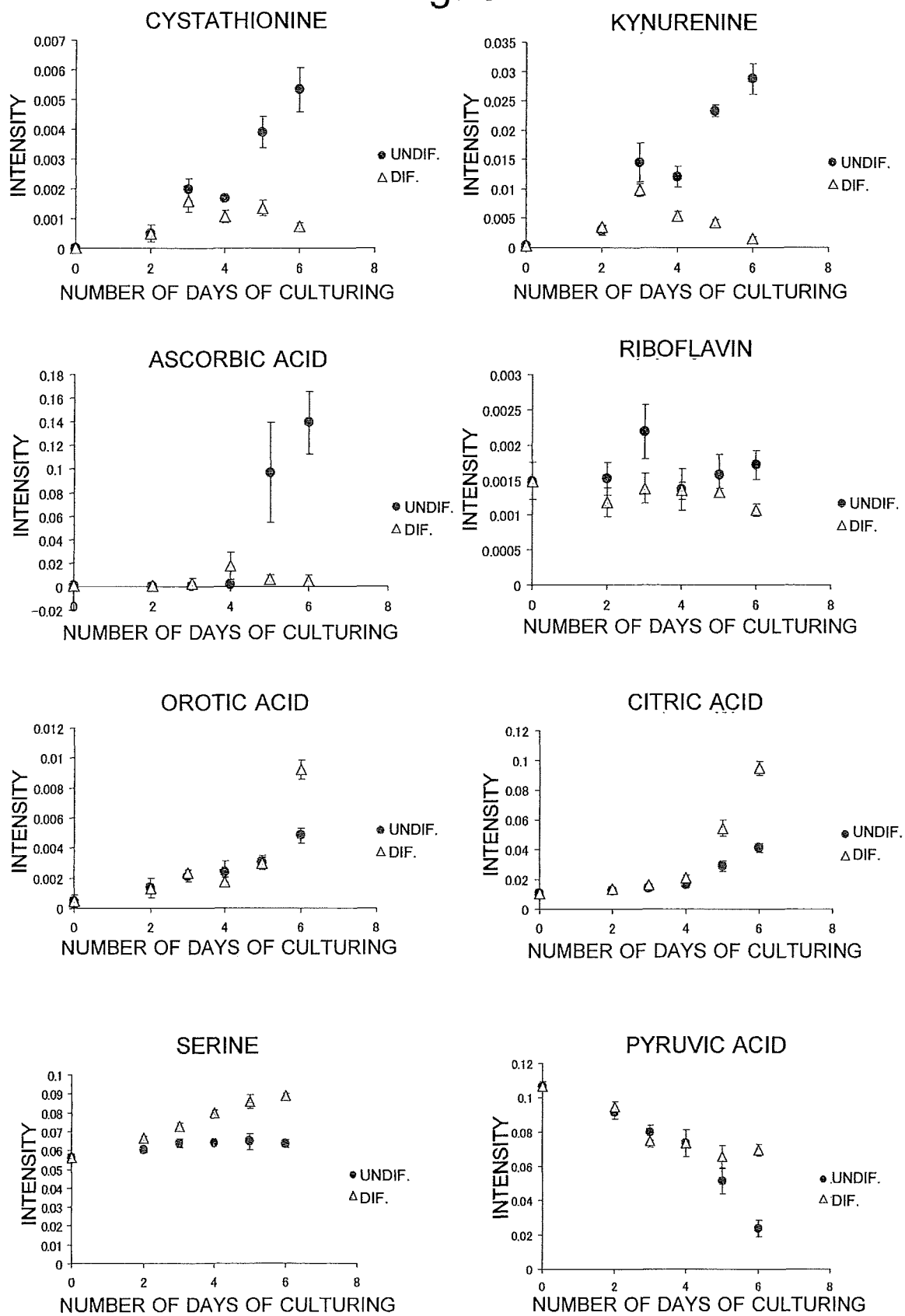
FIG. 3 is a graph showing a temporal change in the amount of various substances determined by an LC-MS analysis of a culture supernatant in the aforementioned example.

FIGS. 2 and 3 show the change in the amount of each of the biomarkers in the culture supernatant over the period from the zeroth to sixth days of the culturing of the KhES-1 line. It should be noted that the results shown in FIG. 2 were obtained by GC-MS analysis, while those shown in FIG. 3 were obtained by LC-MS analysis. As is evident from these figures, it was confirmed that, although there is no difference in the amount of the biomarker compounds between the test cells and the control cells immediately after the beginning of the culturing, the difference in the amount of each biomarker compound between the test cells and the control cells increases with time. Although FIGS. 2 and 3 only show the results obtained for the KhES-1 line, it was also confirmed that the KhES-3 line shows a similar change.

The invention claimed is:

1. A cell differentiation state assessment method, comprising:
    collecting a culture supernatant of test cells cultured in a culture medium;
    replacing the culture medium for the test cells after collecting the test cell supernatant;
    quantitatively analyzing the culture supernatant of the test cells such that an amount of kynurenine in the culture supernatant of the test cells is measured;
    detecting a difference between the amount of kynurenine in the culture supernatant of the test cells and an amount of kynurenine in a culture supernatant of control cells which are pluripotent stem cells and whose state of differentiation is known; and
    detecting a state of differentiation of the test cells based on a result of the difference between the amount of kynurenine in the culture supernatant of the test cells and the amount of kynurenine in a culture supernatant of control cells,
    wherein the test cells are pluripotent stem cells whose state of differentiation is unknown or cells obtained from pluripotent stem cells which have been induced to differentiate, and the detecting of the state of differentiation of the test cells comprises detecting whether the test cells are in an undifferentiated state or to detect whether the test cells include undifferentiated cells.

2. The cell differentiation state assessment method according to claim 1, wherein the control cells are pluripotent stem cells which are unmistakably differentiated, the detecting of the difference between the amounts of kynurenine includes obtaining a ratio of the amount of kynurenine in the supernatant of the test cells to the amount of kynurenine in the supernatant of the control cells, and the detecting of the state of differentiation of the test cells comprises detecting whether the test cells are in an undifferentiated state based on the ratio.

3. The cell differentiation state assessment method according to claim 1, wherein the test cells are pluripotent stem cells whose state of differentiation is unknown, the control cells are pluripotent stem cells which are unmistakably undifferentiated, the detecting of the difference between the amounts of kynurenine includes obtaining a ratio of the amount of kynurenine in the supernatant of the test cells to the amount of kynurenine in the supernatant of the control cells, and the detecting of the state of differentiation of the test cells comprises detecting whether the test cells are in an undifferentiated state based on the ratio.

4. The cell differentiation state assessment method according to claim 1, wherein the quantitatively analyzing is carried out by at least one of an LC-MS and a GC-MS.

5. The cell differentiation state assessment method according to claim 2, wherein the quantitatively analyzing is carried out by at least one of an LC-MS and a GC-MS.

6. The cell differentiation state assessment method according to claim 3, wherein the quantitatively analyzing is carried out by at least one of an LC-MS and a GC-MS.

7. The cell differentiation state assessment method according to claim 2, further comprising:
    replacing the culture medium for the test cells and a culture medium for the control cells after the collecting of the culture supernatant of the test cells; and
    repeating the collecting and analyzing of the culture supernatant of the test cells, the detecting of the difference, and the detecting of the state of differentiation.

8. The cell differentiation state assessment method according to claim 3, further comprising:
    replacing the culture medium for the test cells and a culture medium for the control cells after the collecting of the culture supernatant of the test cells; and
    repeating the collecting and analyzing of the culture supernatant of the test cells, the detecting of the difference, and the detecting of the state of differentiation.

9. The cell differentiation state assessment method according to claim 1, wherein the control cells are pluripotent stem cells which are unmistakably differentiated.

10. The cell differentiation state assessment method according to claim 1, wherein the control cells are pluripotent stem cells which are unmistakably undifferentiated.

11. The cell differentiation state assessment method according to claim 9, further comprising:
    replacing the culture medium for the test cells and a culture medium for the control cells after the collecting of the culture supernatant of the test cells; and
    repeating the collecting and analyzing of the culture supernatant of the test cells, the detecting of the difference, and the detecting of the state of differentiation.

12. The cell differentiation state assessment method according to claim 10, further comprising:
    replacing the culture medium for the test cells and a culture medium for the control cells after the collecting of the culture supernatant of the test cells; and
    repeating the collecting and analyzing of the culture supernatant of the test cells, the detecting of the difference, and the detecting of the state of differentiation.

13. The cell differentiation state assessment method according to claim 1, wherein the test cells are cells obtained from pluripotent stem cells which have been induced to differentiate, the control cells are pluripotent stem cells which are unmistakably differentiated, the detecting of the difference between the amounts of kynurenine includes obtaining a ratio of the amount of kynurenine in the supernatant of the test cells to the amount of kynurenine in the supernatant of the control cells, and the detecting of the state of differentiation of the test cells comprises detecting whether the test cells include undifferentiated cells based on the ratio.

14. The cell differentiation state assessment method according to claim 1, wherein the test cells are cells obtained from pluripotent stem cells which have been induced to differentiate, the control cells are pluripotent stem cells which are unmistakably undifferentiated, the detecting of the difference between the amounts of kynurenine includes obtaining a ratio of the amount of kynurenine in the supernatant of the test cells to the amount of kynurenine in the supernatant of the test control, and the detecting of the state of differentiation of the test cells comprises detecting whether the test cells include undifferentiated cells based on the ratio.

15. The cell differentiation state assessment method according to claim 13, wherein the quantitatively analyzing is carried out by at least one of an LC-MS and a GC-MS.

16. The cell differentiation state assessment method according to claim 14, wherein the quantitatively analyzing is carried out by at least one of an LC-MS and a GC-MS.

17. The cell differentiation state assessment method according to claim 13, further comprising:
replacing the culture medium for the test cells and a culture medium for the control cells after the collecting of the culture supernatant of the test cells; and
repeating the collecting and analyzing of the culture supernatant of the test cells, the detecting of the difference, and the detecting of the state of differentiation.

18. The cell differentiation state assessment method according to claim 14, further comprising:
replacing the culture medium for the test cells and a culture medium for the control cells after the collecting of the culture supernatant of the test cells; and
repeating the collecting and analyzing of the culture supernatant of the test cells, the detecting of the difference, and the detecting of the state of differentiation.

19. The cell differentiation state assessment method according to claim 15, further comprising:
replacing the culture medium for the test cells and a culture medium for the control cells after the collecting of the culture supernatant of the test cells; and
repeating the collecting and analyzing of the culture supernatant of the test cells, the detecting of the difference, and the detecting of the state of differentiation.

* * * * *